(12) United States Patent
Roso et al.

(10) Patent No.: US 7,670,614 B2
(45) Date of Patent: Mar. 2, 2010

(54) USE OF ALKYLPOLYGLYCOSIDES AS EMULSIFYING AGENTS FOR THE PREPARATION OIL-IN-WATER EMULSIONS CONTAINING MINERAL PIGMENTS OR FILLERS AND THE OIL-IN-WATER EMULSIONS CONTAINING SUCH ALKYLPOLYGLYCOSIDES

(75) Inventors: Alicia Roso, Saix (FR); Chantal Amalric, Blan (FR); Nelly Michel, Maisons-Alfort (FR); Jean-Pierre Boiteux, Saix (FR); Hervé Rolland, Castres (FR); Guy Tabacchi, Paris (FR); Alain Milius, Nice (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 1679 days.

(21) Appl. No.: 10/493,726

(22) PCT Filed: Oct. 22, 2002

(86) PCT No.: PCT/FR02/03609

§ 371 (c)(1),
(2), (4) Date: Apr. 23, 2004

(87) PCT Pub. No.: WO03/035657

PCT Pub. Date: May 1, 2003

(65) Prior Publication Data

US 2004/0241127 A1 Dec. 2, 2004

(30) Foreign Application Priority Data

Oct. 25, 2001 (FR) .................................. 01 13808

(51) Int. Cl.
*A61K 8/02* (2006.01)
*A61K 31/70* (2006.01)
(52) U.S. Cl. .................. 424/401; 514/25; 514/844; 514/845
(58) Field of Classification Search .............. 514/844, 514/845, 25; 424/401
See application file for complete search history.

(56) References Cited

U.S. PATENT DOCUMENTS

| | | | |
|---|---|---|---|
| 5,605,651 A * | 2/1997 | Balzer | ......................... 424/401 |
| 5,739,301 A | 4/1998 | Oftring et al. | |
| 6,335,025 B1 * | 1/2002 | Lorant | ......................... 424/401 |
| 6,667,396 B2 | 12/2003 | Milius et al. | |

FOREIGN PATENT DOCUMENTS

| | | |
|---|---|---|
| DE | 196 32 044 A1 | 2/1997 |
| EP | 0 507 047 A2 | 1/1992 |
| EP | 0 734 762 A1 | 10/1995 |
| FR | 2 807 435 A1 | 4/2000 |
| WO | WO 95/22551 | 2/1995 |
| WO | WO 98/22207 | 11/1997 |

OTHER PUBLICATIONS

"Enzymatic glycosylation in the plasticized glass phases: A novel and efficient route to o-glycosides"; I. Gill, et al.; Communications, ed. 2000, 39, No. 21; pp. 3804-3808; XP-002205097.
"Binding of multivalent carbohydrates to concanavalin A and *Dioclea grandiflora* lectin"; T. Dam, et al.; The Journal of Biological Chemistry; vol. 275, No. 19, pp. 14223-14230; XP-002205098, 2000.
"Novel carbohydrate homodimers by olefin metathesis reactions of alkenyl glycosides"; S. Das, et al.; Carbohydrate Letters, vol. 3(5), pp. 361-368; XP-001086664, 1999.
"Synthesis and biological activity of the novel sulfated and phosphorylated bivalent β-D-galactopyranosides containing fatty-alkyl residues"; T. Ikami, et al., Chem. Pharm. Bull. 45(10), vol. 45, No. 10, pp. 1726-1728; XP-000911160, 1997.
Synthesis of sialyl lewis x analogues 2; G. Dekany, et al.; J. Carbohydrate Chemistry 16(1), pp. 11-24; XP-008005688, 1997.
"Preparation of novel oligosaccharides, primers for sugar chain biosynthesis, and their uses"; T. Yamagata, et al.; XP-002205103, 2000.
"Detergent composition with high detergency and foaming properties"; M. Takahashi, et al.; XP-002205104, 1999.
"A convenient synthesis of alkyl D-glycofuranosiduronic acids and alkyl D-glycofuranosides from unprotected carbohydrates"; V. Ferriers, et al.; Carbohydrate Research 311 (1998); pp. 25-35; XP-004142804.
"Glycosidase-catalysed synthesis of glycosides by an improved procedure for reverse hydrolysis: Application to the chemoenzymatic synthesis of galactopyranosyl-(1→4)-$O$-α-galactopyranoside derivatives"; G. Vic, et al.; Tetrahedron: Asymmetry; vol. 7, No. 7, pp. 1973-1985 (1996); XP-0047735.
"Preparation of isoprimeverosides by enzymic transglycosidation"; K. Gijutsuin, et al.; XP-002205105.
"A new synthesis of $O$-glycosides from totally $O$-unprotected glycosyl donors"; V. Ferrieres, et al.; Tetrahedron Letters, vol. 36, No. 16, pp. 2749-2752; XP-004028344.
"Optimization of alkyl β-D-galactopyranoside synthesis from lactose using commercially available β-galactosidases"; D. Stevenson, et al.; Biotechnology and Bioengineering, vol. 42, pp. 657-666; XP-002205101.
"Synthesis of a hexyl methacrylate-terminated disaccharide monomer and study of its radically initiated homo- and copolymerization with styrene"; M. Charreyre, et al.; Makromol. Chem. 194; pp. 117-135; XP-000334531.
"Enzymatic synthesis of alkyl and hydroxyalkyl β-D-mannopyranosides"; N. Taubken, et al.; Short Papers; pp. 517-518; XP-002205102.

* cited by examiner

*Primary Examiner*—Alton N Pryor
(74) *Attorney, Agent, or Firm*—Young & Thompson

(57) ABSTRACT

A composition and process of preparation of emulsifier agents based on an alkylpolyglycoside structure with a length of alkyl chain having from 6 to 12 carbon atoms to be used. The resulting emulsions exhibit an excellent dispersion of the fillers and/or pigments without it being necessary to add coemulsifier or dispersant. The emulsifier makes it possible, by itself alone, to prevent the reagglomeration of the fillers and/or pigments.

2 Claims, No Drawings

USE OF ALKYLPOLYGLYCOSIDES AS EMULSIFYING AGENTS FOR THE PREPARATION OIL-IN-WATER EMULSIONS CONTAINING MINERAL PIGMENTS OR FILLERS AND THE OIL-IN-WATER EMULSIONS CONTAINING SUCH ALKYLPOLYGLYCOSIDES

BACKGROUND of the INVENTION

1. Field of the Invention

A subject-matter of the present invention is the use of specific alkylpolyglycosides as emulsifying agents for the preparation of oil-in-water emulsions comprising inorganic fillers or pigments.

The invention finds application in particular in the cosmetics and pharmaceutical field.

2. Related Art

The formulation of fillers and pigments, in particular of inorganic fillers and pigments, in an emulsion is complex. This is because the presence of fillers or pigments introduces electrical charges into the emulsion which disrupt this emulsion. The latter is difficult to stabilize, often forcing the formulator to use a complex emulsifying system, one or more stabilizers for the aqueous phase, or a dispersing surfactant, to prevent reagglomeration of the fillers over time.

In the case of antisun emulsions, this reagglomeration of the fillers results in a low or unstable UV protecttion factor which decreases over time. In the case of makeup emulsions, reagglomeration of the fillers can also occur, resulting in poor homogeneity of the color in the emulsion itself or when it is applied to the skin. In both these cases, the reagglomeration of the fillers, if it is significant, detrimentally affects the texture of the emulsion, which, instead of appearing smooth and glossy, becomes dull and granular.

To overcome these difficulties, recourse is often had:

- either to complex emulsifying systems, which are generally based on fatty chains with a length of 16 and 18 carbon atoms (saturated, unsaturated or branched);
- or to complex manufacturing processes; for example, inorganic filters with a UV-inhibiting role are very often predispersed in the oil phase or in the water phase.

The problem to be solved thus consists in having available oil-in-water emulsions, comprising inorganic fillers or pigments, which are easy to prepare and which are stable over time, that is to say in which the pigments or fillers do not reagglomerate.

It has now been discovered unexpectedly, and this is the basis of the invention, that an emulsifier based on an alkylpolyglycoside structure with a length of alkyl chain having from 6 to 12 carbon atoms makes it possible to readily formulate oil-in-water (hereinafter "O/W") emulsions comprising inorganic fillers and/or pigments. This result is all the more surprising since short-chain surfactants are not supposed to exhibit good emulsifying properties. These emulsions exhibit an excellent dispersion of the fillers without it being necessary to add coemulsifier or dispersant and without it being useful either to apply specific manufacturing processes as described above. The dispersion obtained with the emulsifier according to the invention is furthermore stable over time, that is to say that, surprisingly, the emulsifier makes it possible, by itself alone, to prevent the reagglomeration of the fillers and/or pigments, including in fluid emulsions such as milks.

SUMMARY OF THE INVENTION

Thus, according to a first aspect, a subject matter of the invention is alkylpolyglycosides represented by the following formulae (Ia) or (Ib):

in which:
X represents the residue of a $C_5$ or $C_6$ sugar, preferably the glucose or xylose residue;
R represents an alkylene or alkylidene group having from 6 to 12 carbon atoms;
r, s and t represent the mean degree of polymerization of each sugar residue. They are greater than 1 and less than or equal to 5, and more particularly less than or equal to 2.5.

DESCRIPTION OF PREFERRED EMBODIMENTS

One aspect of the invention is alkylpolyglycosides represented by the following formulae (Ia) or (Ib):

in which:
X represents the residue of a $C_5$ or $C_6$ sugar, preferably the glucose or xylose residue;
R represents an alkylene or alkylidene group having from 6 to 12 carbon atoms;
r, s, and t represent the mean degree of polymerization of each sugar residue. They are greater than 1 and less than or equal to 5, and more particularly less than or equal to 2.5.

When X represents the xylose residue, r, s and t are more particularly between 1.005 and 1.5.

When X represents the glucose residue, r, s and t are more particularly between 1.05 and 2.

The compounds of formula (Ia) or (Ib) in accordance with the present invention can be prepared by reaction of a reducing sugar and of an alkanediol having from 6 to 12 carbon atoms, preferably hexanediol, octanediol, decanediol or dodecanediol, in desired predetermined proportions.

This reaction results either in the products resulting from the acetalization of one of the two hydroxyl groups of the diol (compounds (Ia)), or in the products resulting from the acetalization of both hydroxyl groups of the diol (compounds (Ib)), or in the mixture of the compounds (Ia) and (Ib).

On an industrial scale, these compounds will preferably be prepared according to one of the two routes conventionally used for the synthesis of alkylpolyglycosides, for example by reaction, in an acidic medium, between the alkanediol having from 6 to 12 carbon atoms and a reducing sugar, such as glucose or xylose.

Such synthetic routes are well known to a person skilled in the art.

If appropriate, this synthesis can be supplemented by neutralization, filtration or decoloration operations or operations for the partial distillation or extraction of the excess diol.

According to a second aspect of the present invention, a subject matter of the latter is a concentrate (C), characterized in that it consists essentially of:

from 30% to 100% by weight of a mixture (M) of at least one compound of formula (IIIa)

$$R_1\text{—}O(X_1)_{p1} \qquad (IIIa)$$

in which $R_1$ represents a linear or branched alkyl radical comprising from 6 to 12 carbon atoms, $X_1$ represents the xylose residue, $p_1$, which represents the mean degree of polymerization of the xylose residue, is a decimal number of greater than 1 and less than or equal to 2.5, and of at least one compound of formula (IIIb)

$$R_2\text{—}O(G)_n \qquad (IIIb)$$

in which $R_2$ represents a linear or branched alkyl radical comprising from 6 to 12 carbon atoms, G represents the glucose residue, n, which represents the mean degree of polymerization of the xylose residue, is a decimal number of greater than 1 and less than or equal to 2.5, and from 0% to 70% by weight of a topically acceptable solvent.

In the concentrate (C) as defined above, the mixture (M) of compounds of formula (IIIa) and of formula (IIIb) is composed essentially:

of 20% to 99% by weight of at least one compound of formula (IIIa), and of 1% to 80% by weight of at least one compound of formula (IIIb).

Examples of topically acceptable solvents are water, alcohols, such as ethanol, propanol or isopropanol, glycols, such as propylene glycol, butylene glycol or hexylene glycol, or water/alcohol or water/glycol mixtures.

According to preferred aspects of the present invention, the concentrate (C) as defined above exhibits one or another or some following specific characteristics:

the concentrate (C) does not comprise solvent;

the concentrate (C) is an aqueous solution of the mixture (M);

the mixture (M) consists essentially of:

from 20% to 30% by weight of at least one compound of the formula (IIIa) and from 70% to 80% by weight of at least one compound of formula (IIIb);

in the formula (IIIa), p is $\geq 1.005$ and $\leq 1.5$;

in the formula (IIIb), n is $\geq 1.05$ and $\leq 2$.

According to a third aspect, a subject matter of the invention is the use of at least one alkylpolyglycoside of formula (Ia) or (Ib) as emulsifying agent for the preparation of oil-in-water emulsions comprising inorganic fillers and/or pigments.

According to a fourth aspect, a subject matter of the invention is the use of at least one alkylpolyglycoside of general formula (II):

$$R\text{—}O(X)_p \qquad (II)$$

in which:

R represents a linear or branched alkyl radical having from 6 to 11 carbon atoms;

X represents the residue of a $C_5$ or $C_6$ sugar, preferably the glucose or xylose residue; and p, which represents the mean degree of polymerization of the sugar residue, is a decimal number of greater than 1 and less than or equal to 5, and more particularly of less than or equal to 2.5, as emulsifying agent for the preparation of oil-in-water emulsions comprising inorganic fillers and/or pigments.

In the formula R—O—$(X)_p$, the R—O— group is bonded to X via the anomeric carbon of the sugar residue, so as to form an acetal functional group.

When X represents the xylose residue, p is more particularly between 1.005 and 1.5.

When X represents the glucose residue, p is more particularly between 1.05 and 2.

The compound of formula R—O—$(X)_p$ can be prepared according to methods well known to a person skilled in the art.

The alkylpolyglycosides in the concentrate (C) in accordance with the invention make it possible to prepare oil-in-water (O/W) emulsions comprising inorganic fillers and/or pigments.

They advantageously represent from 0.2 to 10% by weight, preferably from 0.5 to 5% by weight, of the O/W emulsion.

The inorganic fillers and/or pigments can be lamellar or spherical and without specific limitation with respect to the particle size. Mention may in particular be made, as examples of inorganic fillers and pigments, of titanium dioxide; zinc oxide; iron oxide (black, red or yellow); iron titanate; carbon black; chromium oxide; chromium hydroxide; zirconium oxide; cerium oxide; cobalt titanate; ultramarine; Prussian blue; titanium oxide-coated mica; bismuth oxychloride; pearl essence; talc; aluminum powder; copper powder; gold powder; mica; sericite; boron nitride; photochromic pigments; or interferential pigments. These fillers may have been subjected to a surface treatment or may be encapsulated, such as, for example, in nylon matrices or polymers.

These fillers and pigments generally represent from 0.5 to 40% by weight, preferably from 2 to 25% by weight, of the O/W emulsion.

The O/W emulsion also comprises from 1 to 50% by weight, preferably from 5 to 35% by weight and more preferably from 5 to 25% by weight of a fatty phase composed of one or more oils and/or of one or more waxes.

The oil is advantageously chosen from the following oils:

oils of vegetable origin, such as sweet almond oil, coconut oil, castor oil, jojoba oil, olive oil, rapeseed oil, peanut oil, sunflower oil, wheat germ oil, corn germ oil, soybean oil, cottonseed oil, alfalfa oil, poppy oil, pumpkin-seed oil, evening primrose oil, millet oil, barley oil, rye oil, safflower oil, candlenut oil, passionflower oil, hazelnut oil, palm oil, karite butter, apricot kernel oil, calophyllum oil, sisymbrium oil, avocado oil or calendula oil;

vegetable oils and their methyl esters which are ethoxylated;

oils of animal origin, such as squalene or squalane;

mineral oils, such as liquid paraffin, liquid petrolatum and isoparaffins;

synthetic oils, in particular fatty acid esters, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, or fatty acid monoglycerides, diglycerides and triglycerides, such as glyceryl triheptanoate, alkyl benzoates, poly-α-olefins, polyolefins, such as polyisobutene, synthetic isoalkanes, such as isohexadecane or isododecane, perfluorinated oils and silicone oils.

This oil can also be chosen from fatty acids, fatty alcohols, waxes of natural or synthetic origin and more generally still any fatty substance of vegetable, animal or synthetic origin.

The wax is advantageously chosen from fatty substances which are solid at ambient temperature, such as, for example, beeswax; carnauba wax; candelilla wax; ouricury wax; Japan wax; cork fiber or sugarcane wax; paraffin waxes; lignite waxes; microcrystalline waxes; lanolin wax; ozokerite; polyethylene wax; hydrogenated oils; silicone waxes; vegetable waxes; fatty alcohols and fatty acids which are solid at ambient temperature; or glycerides which are solid at ambient temperature.

The O/W emulsion in accordance with the invention can also comprise up to 10% by weight, for example from 0.1 to 10% by weight, of a stabilizing system.

The stabilizing system can be composed of one or more compounds chosen from magnesium silicate; aluminum silicate; sodium silicate; xanthan gum; acacia gum; locust bean gum; scleroglucan gum; gellan gum; alginates; cellulose and cellulose derivatives; clays; starches and starch derivatives; carbomer; acrylic acid polymers and copolymers; acryloyldimethyl taurate polymers and copolymers; polyvinylpyrrolidone; acrylamide polymers and copolymers; or polyurethanes.

The O/W emulsion can also comprise up to 30% by weight of one or more additives generally used in cosmetics and chosen from:
- coemulsifiers, such as, for example, fatty acids and fatty acid soaps; ethoxylated fatty acids; fatty acid esters; ethoxylated fatty acid esters, including polysorbates; polyglycerol esters; sucrose esters; alkylpolyglycosides with a chain length of greater than 12 carbon atoms; ethoxylated fatty alcohols; sulfated fatty alcohols; or phosphated fatty alcohols;
- preservatives generally used in cosmetics;
- fragrances or other additives with a scenting function (such as, in particular, essential oils and essential waxes);
- cosmetic active principles;
- cosolvents, such as, for example, glycerol; sorbitol; PEG; monopropylene glycol; butylene glycol; isoprene glycol; 2-methyl-1,3-propanediol; ethanol; or hexylene glycol;
- inorganic or organic bases, such as, for example, sodium hydroxide; potassium hydroxide; ammonia; triethanolamine; tetrahydroxypropylethylenediamine; trishydroxyaminomethane; or aminomethylpropanol;
- acids, in particular lactic acid, citric acid, acetic acid or tartaric acid.

Thus, according to a fifth aspect, a subject matter of the present invention is an oil-in-water emulsion comprising at least one alkylpolyglycoside corresponding in particular to the formula (Ia), (Ib) or (II), and pigments and/or fillers.

According to a sixth aspect of the present invention, a subject matter of the latter is an oil-in-water emulsion comprising from 0.5% to 10% by weight and more particularly from 1% to 5% by weight of the concentrate (C) as defined above, and inorganic pigments and/or fillers.

The O/W emulsion in accordance with the invention can be prepared by processes known to a person skilled in the art, such as, for example, a process which comprises the following stages:

$a_1$) The aqueous phase comprising the fillers is milled using, for example, a bead mill or a device with a rotor-stator turbine mixer of Silverson type. This aqueous phase is subsequently heated to a temperature of 70 to 85° C.

$b_1$) At the same time, the fatty phase, comprising the emulsifier and the oils, is heated to an identical temperature of 70 to 85° C.

$c_1$) The compositions according to the invention are introduced without distinction into the fatty phase or the aqueous phase.

$d_1$) The two phases are subsequently mixed and emulsified using, for example, a rotor-stator emulsifying device (for example, a laboratory mixer of Silverson type). After emulsifying for a few minutes, the emulsion is cooled with moderate stirring.

Another example of the process for the preparation of the O/W emulsion comprises the following stages:

$a_2$) The aqueous phase is heated to 70-85° C.

$b_2$) The fatty phase, comprising the fillers, emulsifier and the oils, is heated to an identical temperature of 70 to 85° C.

$c_2$) The compositions according to the invention are introduced without distinction into the fatty phase or the aqueous phase.

$d_2$) The two phases are subsequently mixed and emulsified using, for example, a rotor-stator emulsifying device (Silverson laboratory mixer). After emulsifying for a few minutes, the emulsion is cooled with moderate stirring.

It is also possible, provided all the constituents of the emulsion are liquid at ambient temperature, to prepare said emulsion by a process devoid of heating.

According to a final aspect of the present invention, a subject matter of the latter is a process for the preparation of a cosmetic or pharmaceutical oil-in-water emulsion for topical use, characterized in that between 0.2% and 10% by weight and more particularly between 0.5% and 5% by weight of a concentrate (C) as defined above is mixed with the other constituents of said composition.

EXAMPLES

The invention is illustrated by the nonlimiting examples below. In these examples, the emulsions prepared are monitored:
- by monitoring using a microscope with a magnification of 40.
- by visual (macroscopic) monitoring of the stability of the emulsions with checking after 3 months of the appearance of the emulsions in the flask: smooth or granular appearance, glossy or matt appearance, monitoring of phenomena of phase separation, of release of pigments at the surface of the emulsion or of stratification of the pigments with a nonuniform visual effect. The optimum criteria are a glossy, perfectly smooth and homogeneous emulsion without phase separation or release or stratification of the pigments and fillers. The grading is as follows: + if all the criteria are satisfactory, +/− if at least one of the criteria is unsatisfactory, 0 if none of the criteria is satisfactory.
- by monitoring of the texture with the preparation, on a Plexiglas® sheet, of films calibrated to 120 μm and checking for the absence of agglomerates of fillers and pigments. The grading is as follows: + in the absence of specks 3 months after the manufacture of the emulsion, +/− in the presence of a few specks, 0 in the presence of numerous specks.

In the case of the emulsions comprising fillers with the role of protecting from UV radiation, the protection factor is evaluated according to the method described below:

The protection factor is evaluated in vitro by measuring the absorbing power with respect to UV-B and UV-A radiation after spreading a film of emulsion over a support which models the skin surface.

The emulsion is spread in a calibrated way (2 mg/cm$^2$) over a prehydrated collagen matrix sold under the name Vitroskin® by IMS. After drying the film for a period of 15 minutes, the coated support is subjected to exposure to UV radiation using a Labsphere® spectrophotometer. The sun protection coefficient is calculated by the software of the device according to the Diffey formula from the transmission of the UV radiation over the whole spectrum between 280 and 400 nm.

In view of the role of UV-A radiation in the onset of skin cancers, the relative importance of the protection with respect to UV-A radiation is calculated by producing the ratio of the area under the absorbance curve in the UV-A spectrum to the area under the absorbance curve in the UV-B spectrum. A UV-A/UV-B ratio of >0.6 is recommended for effective protection with respect to UV-A radiation.

Example 1

Preparation of an Alkylpolyxyloside of Formula (I)

908.4 g of 1,10-decanediol, sold by Cognis under the name Speziol® C10/2, are gradually introduced into a two liter glass reactor. The reactor is brought to a temperature of 90° C., so as to effectively melt the 1,10-decanediol, stirring is started and 390.0 g of xylose are dispersed in the presence of a catalytic amount of sulfuric acid. After two hours at 80° C./85° C. under vacuum and neutralization with sodium hydroxide, the product exhibits the following analytical characteristics:

Appearance (visual): off-white solid
Color of a molten product (NFT 20 030): 1 vcs
pH of a 5% dispersion (NFT 73 206): 7.8
Water content: 0.47%
Acid number (NFT 60 204): 0.25
Hydroxyl number: 689
Residual 1,10-decanediol: 37.3%

Example 2

Preparation of an Alkylpolyxyloside of Formula (I)

The procedure of example 1 is repeated but 500.6 g of 1,10-decanediol being reacted with 430 g of xylose to result in a product exhibiting the following analytical characteristics:

Appearance (visual): black solid
pH of a 5% dispersion (NFT 73 206): 7.8
Water content: 2.0%
Acid number (NFT 60 204): 4.9
Hydroxyl number: 726
Residual 1,10-decanediol: 9.0%

Example 3

Preparation of O/W Emulsions Intended for UV Protection

O/W emulsions are prepared which comprise the following ingredients:

| | | |
|---|---|---|
| A | Emulsifier | 02.50% |
| | $C_{12}$–$C_{15}$ Alkyl benzoate | 20.00% |
| | Titanium oxide (20 nm/dimethicone coating) | 10.00% |
| B | Cyclomethicone | 05.00% |
| | Glycerol | 07.00% |
| C | Tetrasodium EDTA | 00.20% |
| | Water | q.s. for 100% |
| | Carbomer ® | 00.05% |
| | Tromethamine | q.s. pH > 7 |
| | Magnesium silicate/Aluminum silicate | 01.00% |
| | Xanthan gum | 00.15% |
| D | DL-α-Tocopherol | 00.05% |
| | Preservatives | q.s. |

The Carbomer®, the magnesium silicate/aluminum silicate and the xanthan gum are dispersed in the aqueous phase. The aqueous phase is heated to 70-85° C. and then the EDTA and the tromethamine are added.

The fatty phase, comprising the titanium oxide, the emulsifier and the $C_{12}$-$C_{15}$ alkyl benzoate, is heated to an identical temperature of 70 to 85° C. The cyclomethicone and the glycerol are added to this hot fatty phase.

The two phases are subsequently mixed and emulsified using a rotor-stator emulsifying device (Silverson laboratory mixer). After emulsifying for a few minutes, the emulsion is cooled with moderate stirring.

The tocopherol and the preservatives are added at the end of cooling with moderate stirring.

The results are presented in table 1.

TABLE 1

| Emulsifier | Texture of the emulsion | Brookfield viscosity (mPa · s) | Stability at AT | Microscopic appearance of the emulsion |
|---|---|---|---|---|
| Decylglucoside (p = 1.45) | Smooth milk | 9500 | >3 months | Fine and homogeneous |
| Decylglucoside (p = 1.9) | Smooth milk | 7000 | >3 months | Fine and homogeneous |
| Example 1 | Smooth milk | 9000 | >3 months | Fine and homogeneous |
| Ethylhexyl-glucoside (p = 1.45) | Smooth milk | 10 500 | >3 months | Fine and homogeneous |

Comparative Example 1

The procedure of example 3 is repeated by using alkylpolyglucoside-based emulsifiers having a chain with 4 and 12 carbon atoms and ethoxylated emulsifiers. The results are presented in table 2.

TABLE 2

| Emulsifier | Texture of the emulsion | Brookfield viscosity (mPa · s) | Stability at AT | Microscopic appearance of the emulsion |
|---|---|---|---|---|
| Cetearyl-glucoside (p = 1.25) | Granular cream | 43 000 | >3 months | agglomerates |
| Dodecyl-glucoside (p = 1.43) | Granular milk | 7000 | <7 days | agglomerates |
| Butyl-glucoside (p = 1.45) | Non-emulsifying | — | — | — |

TABLE 2-continued

| Emulsifier | Texture of the emulsion | Brookfield viscosity (mPa · s) | Stability at AT | Microscopic appearance of the emulsion |
|---|---|---|---|---|
| Laureth-7 | Granular | 15 000 | <3 months | agglomerates |
| Deceth-4 | Granular milk | 8000 | <7 days | agglomerates |
| Deceth-5 | Granular cream | 11 000 | <7 days | agglomerates |
| Deceth-3 | Non-emulsifying | — | — | — |

It is not possible with butylglucoside to obtain an emulsion and dodecylglucoside results in emulsions which are less stable than those obtained with the alkylglucosides according to the invention. Cetearyl-glucoside and dodecylglucoside give agglomerates. The ethoxylated nonionic surfactants are less effective than the alkylpolyglycosides according to the invention.

Example 4

Stability Over Time of the Dispersion of Pigments and of the Protection Factor of O/W Emulsions An emulsion is prepared which comprises the following ingredients:

| | | |
|---|---|---|
| A | Emulsifier | 2.50% |
| | Diisopropyl adipate | 25.00% |
| | Titanium oxide (20 nm/dimethicone coating) | 10.00% |
| | Zinc oxide (50 nm) | 02.00% |
| B | Cyclomethicone | 03.00% |
| | Glycerol | 07.00% |
| C | Tetrasodium EDTA | 00.20% |
| | Water | q.s. for 100% |
| | Carbomer ® | 00.05% |
| | Tromethamine | q.s. pH > 7 |
| | Magnesium silicate/Aluminum silicate | 01.00% |
| | Xanthan gum | 00.15% |
| D | DL-α-Tocopherol | 00.05% |
| | Preservatives | q.s. |

The Carbomer®, the magnesium silicate/aluminum silicate and the xanthan gum are dispersed in the aqueous phase. The aqueous phase is heated to 70-85° C. and then the EDTA and the tromethamine are added.

The fatty phase, comprising the titanium oxide and the zinc oxide, the emulsifier and the oil, is heated to an identical temperature of 70 to 85° C. The cyclomethicone and the glycerol are added to this hot fatty phase.

The two phases are subsequently mixed and emulsified using a rotor-stator emulsifying device (Silverson laboratory mixer). After emulsifying for a few minutes, the emulsion is cooled with moderate stirring.

The tocopherol and the preservatives are added at the end of cooling with moderate stirring.

The results are presented in table 3.

TABLE 3

| Emulsifier | Decylglucoside (invention) | (PEG 100 stearate + glycerol stearate) 1.7% + DEA cetyl phosphate 0.8% (comparative) | Dodecyl-glucoside (comparative) |
|---|---|---|---|
| Texture of the emulsion | Smooth milk >1 year | Granular milk at 1 month | Granular milk at 1 day |
| Microscopic appearance | Fine and homogeneous dispersion >1 year | Onset of agglomerates beyond 15 days | Onset of agglomerates at 1 day |
| Stability | | | |
| AT | >1 year | >1 year | <1 month |
| 40° C. | >6 months | <3 months | <1 month |
| 50° C. | >1 month | <15 days | <1 month |
| Protection factor | | | |
| 7 days | 14 | 15 | 8 |
| 1 month | 16 | 8 | — |
| 1 year | 15 | 5 | — |
| UV-A/UV-B Ratio | | | |
| 7 days | 0.9 | 0.9 | 0.55 |
| 1 year | 0.9 | 0.6 | — |

Decylglucoside, the emulsifier according to the invention, makes it possible, in contrast to the comparative emulsifiers, to retain a fine and homogeneous dispersion of the fillers during the storage with consequently a visual texture which remains perfectly smooth over time and a stable protection factor, both in the UV-B spectrum and in the UV-A spectrum, as is illustrated by the value of the factor and that of the UV-A/UV-B ratio.

Example 5

Preparation of an O/W Emulsion without Heating

An emulsion is prepared which comprises the following ingredients:

| | | |
|---|---|---|
| A | Emulsifier | 03.00% |
| | Caprylic/capric triglycerides | 20.00% |
| | Zinc oxide | 05.00% |
| | Glycerol | 05.00% |
| C | Tetrasodium EDTA | 00.10% |
| | Water | q.s. for 100% |
| | Sepigel ® 305 | 01.50% |
| | Tromethamine | q.s. pH > 7 |
| | Magnesium silicate/Aluminum silicate | 01.00% |
| | Xanthan gum | 00.15% |
| D | DL-α-Tocopherol | 00.05% |
| | Preservatives | q.s. |

The Sepigel® 305 (polyacrylamide and $C_{11}$-$C_{13}$ isoparaffin and laureth-7; sold by Seppic), the magnesium silicate/aluminum silicate and the xanthan gum are dispersed in the aqueous phase. The EDTA and the tromethamine are added to the aqueous phase.

The fatty phase is produced by simple mixing of the constituents without heating.

The two phases are subsequently mixed and emulsified using a rotor-stator emulsifying device (Silverson laboratory mixer). The tocopherol and the preservatives are added with moderate stirring.

The results are presented in table 4.

TABLE 4

| Emulsifier | Decylglucoside | Octylxyloside |
|---|---|---|
| Texture of the emulsion | Smooth milk | Smooth milk |
| Microscopic appearance | Fine and homogeneous dispersion | Fine and homogeneous dispersion |
| Stability | | |
| AT | >1 month | >1 month |
| 40° C. | >1 month | >1 month |
| 50° C. | >1 month | >1 month |
| Protection factor | | |
| 1 month | 9 | 6 |
| 1 year | 8.5 | 6 |

Example 6

Preparation of Emulsions Intended for Makeup

| A | Emulsifier | 2.50% |
|---|---|---|
| | Isononyl isononanoate | 08.00% |
| | Diisopropyl dimer dilinoleate | 08.00% |
| B | Cyclomethicone | 04.00% |
| | Sepigel ® 305 | 01.50% |
| C | Water | q.s. for 100% |
| | Micropearl ® M305 (crosslinked methyl methacrylate polymer) | 02.00% |
| | Tetrasodium EDTA | 00.50% |
| D | Pigment paste | |
| | Butylene glycol | 04.00% |
| | Polyethylene glycol 400 | 04.00% |
| | Titanium dioxide, E171 | 07.00% |
| | Talc, Luzenac 000C | 02.00% |
| | Yellow iron oxide, Sicovit yellow 10 E172 | 00.80% |
| | Red iron oxide, Sicovit red 30 E172 | 00.30% |
| | Black iron oxide, Sicovit black | 00.05% |
| | Water | 20.00% |
| | NaOH | q.s. for pH > 8 |
| E | Preservatives | q.s. |
| | Fragrance | 00.20% |

The pigment paste is milled beforehand on a bead mill.

The water is heated to 70-75° C. and then the Micropearl®, the EDTA and the pigment paste are added to the hot aqueous phase.

The fatty phase, comprising the emulsifier and the oils, is heated to a temperature of 70 to 75° C. The cyclomethicone and the Sepigel® 305 are added to this hot fatty phase.

The two phases are subsequently mixed and emulsified using a rotor-stator emulsifying device (Silverson laboratory mixer). After emulsifying for a few minutes, the emulsion is cooled with moderate stirring.

The preservatives and the fragrance are added at the end of cooling with moderate stirring.

The results are presented in table 5.

TABLE 5

| Emulsifier | Decylglucoside (invention) | Cetearyl-glucoside (comparative) | Sodium stearate 1.7% + Steareth-10 0.8% (comparative) |
|---|---|---|---|
| Visual appearance after 3 months | + | +/− | +/− |
| Texture after 3 months | + | +/− | 0 |
| Rendering of the color on application (Minolta CR300 chromameter) after 3 months | | | |
| Parameter L | 68.3 (±0.7) | 70.1 (±0.4) | 73.4 (±0.6) |
| Parameter a | 2.3 (±0.6) | 18.2 (±2.3) | 16.5 (±2.7) |
| Parameter b | 30 (±0.9) | 23.7 (±1.5) | 20.2 (±2.8) |

The fineness of the dispersion of the fillers is reflected by an improvement in the spreading over the skin, by uniform color and by a better rendering of the color on the skin: decrease in the whiteness (parameter L) and an enhancement in the colored parameters a (red hue) and b (blue hue). The non-uniformity in the color with the comparative examples is clearly apparent with regard to the standard deviation values for a and b, which are higher than in the example according to the invention.

Example 7

Preparation of O/W Emulsions Intended for Makeup

| A | Isononyl isononanoate | 08.00% |
|---|---|---|
| | Triisostearyl citrate | 08.00% |
| | Simulgel ® NS | 04.00% |
| B | Water | q.s. for 100% |
| | Tetrasodium EDTA | 00.05% |
| | Emulsifier | 0.8% |
| C | Pigment paste | |
| | Butylene glycol | 04.00% |
| | Polyethylene glycol 400 | 04.00% |
| | Titanium dioxide, E171 | 05.00% |
| | Yellow iron oxide, Sicovit yellow 10 E172 | 00.80% |
| | Red iron oxide, Sicovit red 30 E172 | 00.30% |
| | Black iron oxide, Sicovit black | 00.05% |
| | Water | 20.00% |
| | NaOH | q.s. for pH > 8 |
| D | Preservatives | q.s. |
| | Fragrance | 00.20% |

The pigment paste is milled beforehand on a bead mill.

The Simulgel® NS (sodium acryloyldimethyl taurate/hydroxyethyl acrylate copolymer and squalane and polysorbate 80; sold by Seppic) is mixed with the oils. The aqueous phase B is added to phase A to form the cream gel. The pigment paste (phase C) and subsequently phase D are then added directly to the cream gel with moderate stirring.

The results are presented in table 6.

TABLE 6

| Emulsifier | Decylglucoside (invention) | Laureth-7 (comparative) |
| --- | --- | --- |
| Visual appearance after 3 months | + | 0 |
| Texture after 3 months | + | 0 |

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An oil-in-water emulsion containing inorganic pigments and/or fillers, further comprising an emulsifier of formula (II)

$$R\text{---}O(X)_p \quad (II)$$

wherein:
a) R represents a linear alkyl radical having from 8 to 10 carbon atoms;
b) X represents the residue of a $C_5$ or $C_6$ sugar; and
c) p is a decimal number greater than 1, and less than or equal to 5.

2. The emulsion of claim 1, which is an antisun or a makeup emulsion.

* * * * *